US012594174B1

(12) United States Patent
    Ingalls

(10) Patent No.: US 12,594,174 B1
(45) Date of Patent: Apr. 7, 2026

(54) MICROMINIATURE PATTERNED METAL ON FLEXING INTERVENTIONAL SURGICAL SUBSTRATES

(71) Applicant: Professional Plating Inc., Anoka, MN (US)

(72) Inventor: Craig A. Ingalls, Burnsville, MN (US)

(73) Assignee: Professional Plating Inc., Anoka, MN (US)

( * ) Notice: Subject to any disclaimer, the term of this patent is extended or adjusted under 35 U.S.C. 154(b) by 835 days.

(21) Appl. No.: 17/699,890

(22) Filed: Mar. 21, 2022

(51) Int. Cl.
    | | |
    |---|---|
    | *A61F 2/92* | (2013.01) |
    | *A61L 31/08* | (2006.01) |
    | *A61L 31/10* | (2006.01) |
    | *A61L 31/14* | (2006.01) |
    | *G05B 19/19* | (2006.01) |
    | *C25D 5/02* | (2006.01) |

(52) U.S. Cl.
    CPC .............. *A61F 2/92* (2013.01); *A61L 31/082* (2013.01); *A61L 31/10* (2013.01); *A61L 31/14* (2013.01); *G05B 19/19* (2013.01); *A61L 2420/02* (2013.01); *A61L 2420/08* (2013.01); *C25D 5/022* (2013.01)

(58) Field of Classification Search
    None
    See application file for complete search history.

(56) References Cited

U.S. PATENT DOCUMENTS

| | | |
    |---|---|---|
    | 4,952,357 A | 8/1990 | Euteneuer |
    | 5,207,700 A | 5/1993 | Euteneuer |
    | 5,352,199 A | 10/1994 | Tower |
    | 5,499,980 A | 3/1996 | Euteneuer |
    | 5,609,606 A | 3/1997 | O'Boyle |
    | 5,611,807 A | 3/1997 | O'Boyle |
    | 5,718,684 A | 2/1998 | Gupta |
    | 5,782,742 A | 7/1998 | Crocker et al. |
    | 5,865,801 A | 2/1999 | Houser |
    | 6,176,821 B1 | 1/2001 | Crocker et al. |
    | 6,500,108 B1 | 12/2002 | Sorensen et al. |
    | 6,572,813 B1 | 6/2003 | Zhang et al. |
    | 6,699,170 B1 | 3/2004 | Crocker et al. |
    | 6,733,513 B2 | 5/2004 | Boyle et al. |

(Continued)

OTHER PUBLICATIONS

English translation JPH05317924 (Year: 1992).*
English translation CN 106400022 (Year: 2016).*
English translation CN107075283 (Year: 2014).*

*Primary Examiner* — Stefanie S Wittenberg
(74) *Attorney, Agent, or Firm* — Shewchuk IP Services, LLC; Jeffrey D. Shewchuk

(57) ABSTRACT

A base interventional surgical device which flexes during use (ISDFU) is coated with powder coated epoxy and cured. Selected areas of the maskant are removed by laser ablation using a computer numerically controlled galvo, while holding/moving the part with a CNC robot so laser ablation can be performed on any surface while that surface is oriented normal to the laser beam. A radiopaque metal is deposited onto the exposed selected areas of the ISDFU by electrolytic deposition. After the metal layer spots are deposited, the remainder of the maskant is removed by dissolving in a solvent. The resultant metal layer(s) do not circumscribe any portion of the ISDFU, and thus do not interfere with flexing of the ISDFU nearly as much as prior art radiopaque marker bands would.

18 Claims, 7 Drawing Sheets

(56)  References Cited

U.S. PATENT DOCUMENTS

| | | | |
|---|---|---|---|
| 6,761,708 B1 | 7/2004 | Chiu et al. | |
| 7,189,229 B2 | 3/2007 | Lopath et al. | |
| 7,264,458 B2 | 9/2007 | Holman et al. | |
| 7,593,778 B2 | 9/2009 | Chandran et al. | |
| 7,708,928 B2 | 5/2010 | Holman et al. | |
| 9,355,441 B2 | 5/2016 | Wersborg et al. | |
| 9,622,680 B2 | 4/2017 | Ghaffari et al. | |
| 9,662,069 B2 | 5/2017 | De Graff et al. | |
| 10,898,691 B2 | 1/2021 | Crall et al. | |
| 2002/0165600 A1 * | 11/2002 | Banas | A61M 25/09 |
| | | | 600/585 |
| 2003/0018381 A1 * | 1/2003 | Whitcher | C23C 14/0005 |
| | | | 427/2.24 |
| 2005/0192663 A1 * | 9/2005 | Lau | A61F 2/89 |
| | | | 623/1.16 |
| 2005/0279642 A1 * | 12/2005 | Brondum | C23C 14/505 |
| | | | 204/198 |
| 2009/0259125 A1 * | 10/2009 | Stinson | A61B 90/39 |
| | | | 600/431 |
| 2011/0276125 A1 * | 11/2011 | Walker | G03F 7/24 |
| | | | 430/320 |
| 2012/0009325 A1 * | 1/2012 | Storment | C25D 5/022 |
| | | | 427/2.25 |
| 2013/0090599 A1 | 4/2013 | Mchugh | |
| 2016/0340786 A1 * | 11/2016 | Mukai | B32B 15/013 |
| 2017/0287770 A1 | 10/2017 | Gangakhedkar et al. | |
| 2018/0229011 A1 | 8/2018 | Govari et al. | |
| 2018/0333281 A1 * | 11/2018 | Tehrani | A61F 2/06 |
| 2019/0060622 A1 | 2/2019 | Beeckler | |
| 2019/0175262 A1 | 6/2019 | Govari et al. | |

* cited by examiner

MICROMINIATURE PATTERNED METAL ON FLEXING INTERVENTIONAL SURGICAL SUBSTRATES

CROSS-REFERENCE TO RELATED APPLICATION(S)

None.

BACKGROUND OF THE INVENTION

Interventional surgery employs catheter-based surgical tools which are generally introduced to the body through very small incisions and moved through the body's vascular system, as compared to traditional open surgical procedures which involve substantially larger incisions and direct access to the surgical site. Interventional procedures are less invasive and generally result in substantially reduced patient trauma and faster recovery times. The present invention is directed to applying metal layers on tissue-compatible substrates which flex during deployment and/or in-situ, particularly for use in the field of radiopaque markers on microminiature devices used in internal health care for interventional surgical deployment by a catheter.

There are many interventional surgical devices which flex during deployment and/or in-situ, with well known examples being stents and certain hypotubes. A stent is a tubular support for use inside a blood vessel, canal, duct or similar human tissue lumen. An exemplary stent is shown in FIGS. 1 and 2. The stent is commonly transported via catheter to the desired deployment site in a compressed (smaller inside and outside diameter) state, possibly requiring twisting and bending as it proceeds through the vascular system to the deployment site. The stent is then released at the deployment site so it expands outwardly against the human tissue lumen. To achieve the desired flexibility and change of shape from the compressed to the expanded configuration, the stent typically includes a mesh of beams or strands, possibly laser cut to achieve the desired small and complex profile. A hypotube is a tube with micro-engineered features along its length, often used in deploying balloons or stents. Many hypotubes involve a similar shape transformation like stents do, from a first shape during transport and flexing to a second shape at deployment. Often the substrate used for stents or hypotubes is a spring metal or shape memory alloy that can be deformed when cold but returns to its pre-deformed shape when heated, with the most commonly used shape memory alloy being Nitinol. The shape and size during transport and the shape and size after deployment are both critical for successful surgical outcomes. Designers of such deployment-flexing interventional surgical devices go to great lengths to engineer the shape and mechanical properties of the nitinol strands, wires, etc. used in the device.

For the best surgical outcomes, exact placement of the interventional surgical device for deployment is also critical, and the surgeon needs to be able to quickly and easily visualize the device (both its transport shape and its later, deployed shape) relative to the surrounding human tissue. Visualization of the surrounding human tissue depends upon the visualization system used and the exact deployment location. With current visualization systems, nitinol-based interventional surgical devices may not appear sufficiently different from the surrounding tissue for the surgeon to have confidence in placement location accuracy at many deployment locations. More particularly, largely due to its relatively low material density compared to other metals, under x-ray imaging nitinol often appears indistinguishable or nearly indistinguishable from human tissue. Accordingly, it is common to add a radiopaque marker, such as out of a high-density, bio-compatible material, to the medical device. Generally, metals most suitable for radiopaque marker applications will have a high density, such as a density of at least 15 gms/cc, and will also be highly bio-inert. Ideal candidates are tungsten, gold, platinum and iridium, osmium, tantalum and rhenium and alloys thereof, with currently preferred metals being gold or platinum.

Many radiopaque markers are separately formed (such as by mechanical fabrication techniques) from the interventional surgical device and then crimped to the interventional surgical device. Other radiopaque markers are formed by depositing (such as through physical vapor deposition) a layer of radiopaque material onto the interventional surgical device. In either case, the radiopaque marker(s) can interfere with the carefully-designed flexing properties and shapes of the interventional surgical device. In particular, radiopaque markers often adversely affect the radial compression behavior of laser cut stents. Other types of interventional surgical devices which display symmetry along the length axis may also have their movement behavior adversely affected by a radiopaque marker. The attachment between the radiopaque marker(s) and the interventional surgical device needs to be sufficiently strong and robust to prevent the radiopaque marker(s) from being dislodged or moved from its (their) location on the interventional surgical device due to the shear forces of insertion of the catheter into the body and/or shear forces occurring during device flexure. Better construction methods and structures for placing one or more radiopaque markers onto interventional surgical devices are needed.

BRIEF SUMMARY OF THE INVENTION

The present invention is method of forming a device, particularly an interventional surgical device which flexes during use (ISDFU), as well as a device formed in accordance with the method. A base ISDFU is provided, perhaps laser cut out of nitinol. At least a significant portion of the base ISDFU is coated with a maskant, such as by powder coating of a polymer layer. Selected areas of the maskant are removed by a computer numerically controlled material removal process. A metal layer, such as of a radiopaque metal, is then deposited onto the exposed selected areas of the ISDFU, such as by electrolytic deposition in which all of the selected areas are simultaneously exposed within the electrolytic solution while the maskant protects the remainder of the base ISDFU which is within the electrolytic solution from metal deposition. After the metal layer spots are deposited, the remainder of the maskant is removed, such as by dissolving in a solvent, while leaving the deposited metal layer intact on the selected areas of the ISDFU. The resultant metal layer(s) do not circumscribe any portion of the ISDFU, and thus do not interfere with flexing of the ISDFU nearly as much as prior art radiopaque marker bands would.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION OF THE PREFERRED EMBODIMENTS

Figure 1:
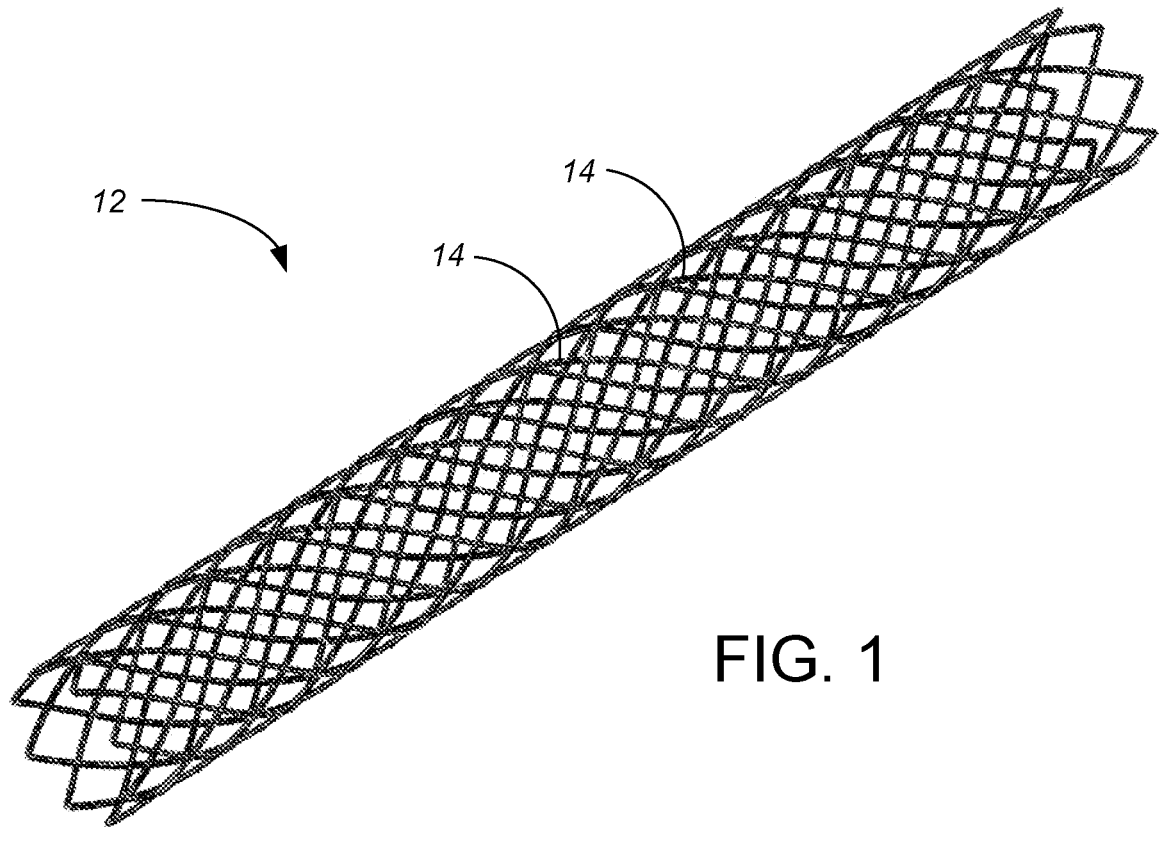
FIG. 1 is a perspective view of a stent for use with the present invention.
Figure 2:
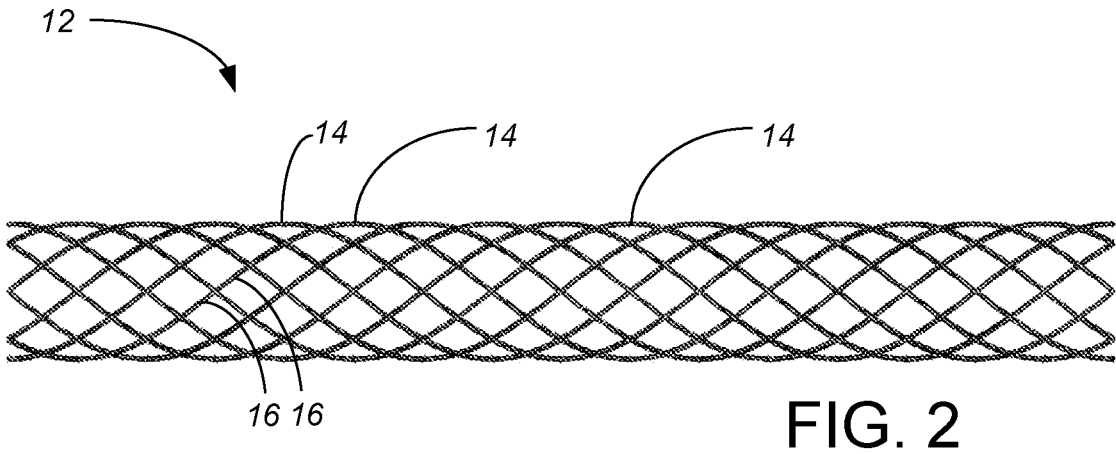
FIG. 2 is a side view of the stent of FIG. 1.

A first step 10 of the method of the present invention is to form, provide or obtain an interventional surgical device which flexes during use ("ISDFU"), with a first example being the stent 12 shown in its expanded state in FIGS. 1 and 2. This stent 12 can be compressed to a smaller outer diameter, and then advanced within the human body (such as through the patient's vascular system) to a deployment location using a catheter (not shown). When released at the deployment location, the stent 12 expands outwardly, such as to hold open a blood vessel for passage of blood through the inner diameter of the stent 12. The design of this particular stent 12 involves a profile laser cut from a tube to define a mesh of sixteen strands 14, eight wound clockwise and eight wound counterclockwise and joined at intersections. The strands 14 essentially form a series of elastic beams 16, which can be bent and/or flexed but spring back toward their relaxed position to bias the blood vessel open.

Being laser cut, each strand/beam 14/16 has a rectangular cross-section, about 0.01 inches or smaller in both thickness and width.

Such stents are well known ISDFUs, and can be formed of a range of materials, with one commonly used material being Nitinol. Nitinol is a metal alloy of nickel and titanium with unique properties, including superelasticity or pseudoelasticity and "shape memory" properties. That means nitinol can "remember" an earlier shape and return to such an earlier shape when heated. Nitinol also shows great elasticity under stress.

At the time of deployment of the stent 12, i.e., when the stent 12 is released from its compressed state to push tissue radially outward, the primary flexing direction of each of the elastic beams 16 is radially inward/outward. For many deployed stents, this radially inward/outward flex at the time of deployment is the only significant flexing of the stent, which thereafter has a relatively fixed shape. Some stents, however, may be deployed at a body location where flexing in a different direction is often required, such as when the patient moves. Moreover, other types of ISDFUs, such as ISDFUs implanted at or near a heart valve, may have a primary flexing which occurs not only at the time of deployment but also after implantation, again involving a primary flexing direction which may be other than radially inward/outward. Still other ISDFUs are flexed only while attached with the catheter, and may be removed from the human body before the surgery is concluded. Nonetheless, in the design of any ISDFU for its intended deployment location within the body and its intended use, a primary flexing direction can generally be identified.

When using common imaging or visualization systems (not shown) such as based on x-rays, nitinol has a radiodensity similar to human tissue at many deployment locations, i.e., does not show up well to the surgeon viewing the visualization screen (not shown). For ISDFUs formed of nitinol or other materials of similar radiodensity, it is common to add one or more radiopaque markers. The primary intent of the present invention is to add one or more radiopaque markers to an ISDFU which minimally affects flexing in the primary flexing direction of the ISDFU.

Figure 3:
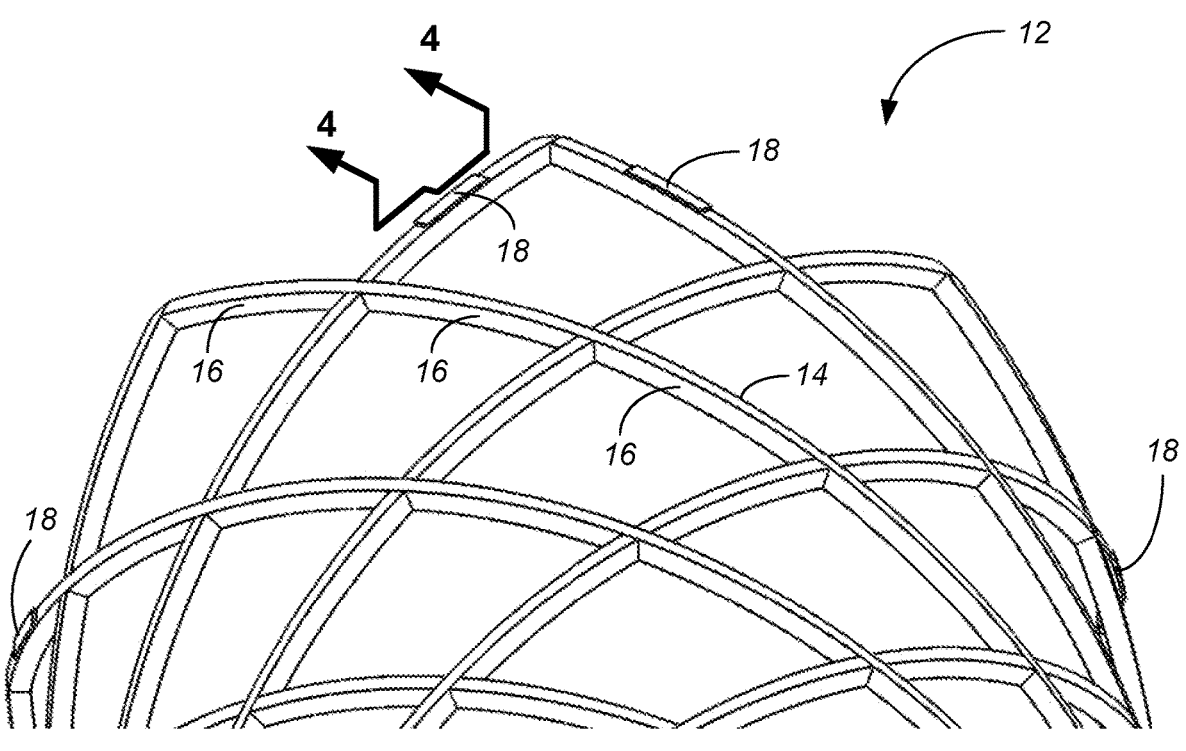
FIG. 3 is a perspective view of the end of the stent of FIGS. 1 and 2 after application of the present invention to add radiopaque markers.
Figure 4:
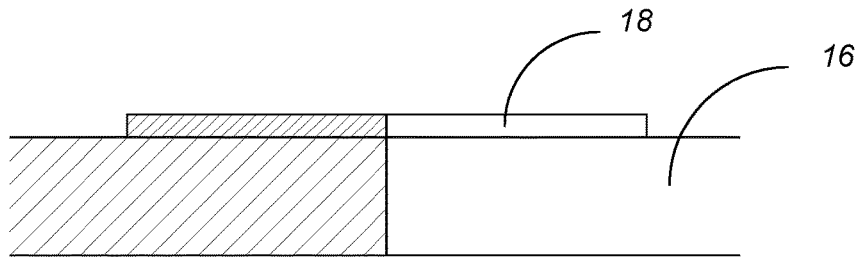
FIG. 4 is a cross-sectional/side view of a portion of the stent of FIG. 3, taken along the cut lines 4-4 in FIG. 3.
Figures 5, 6:
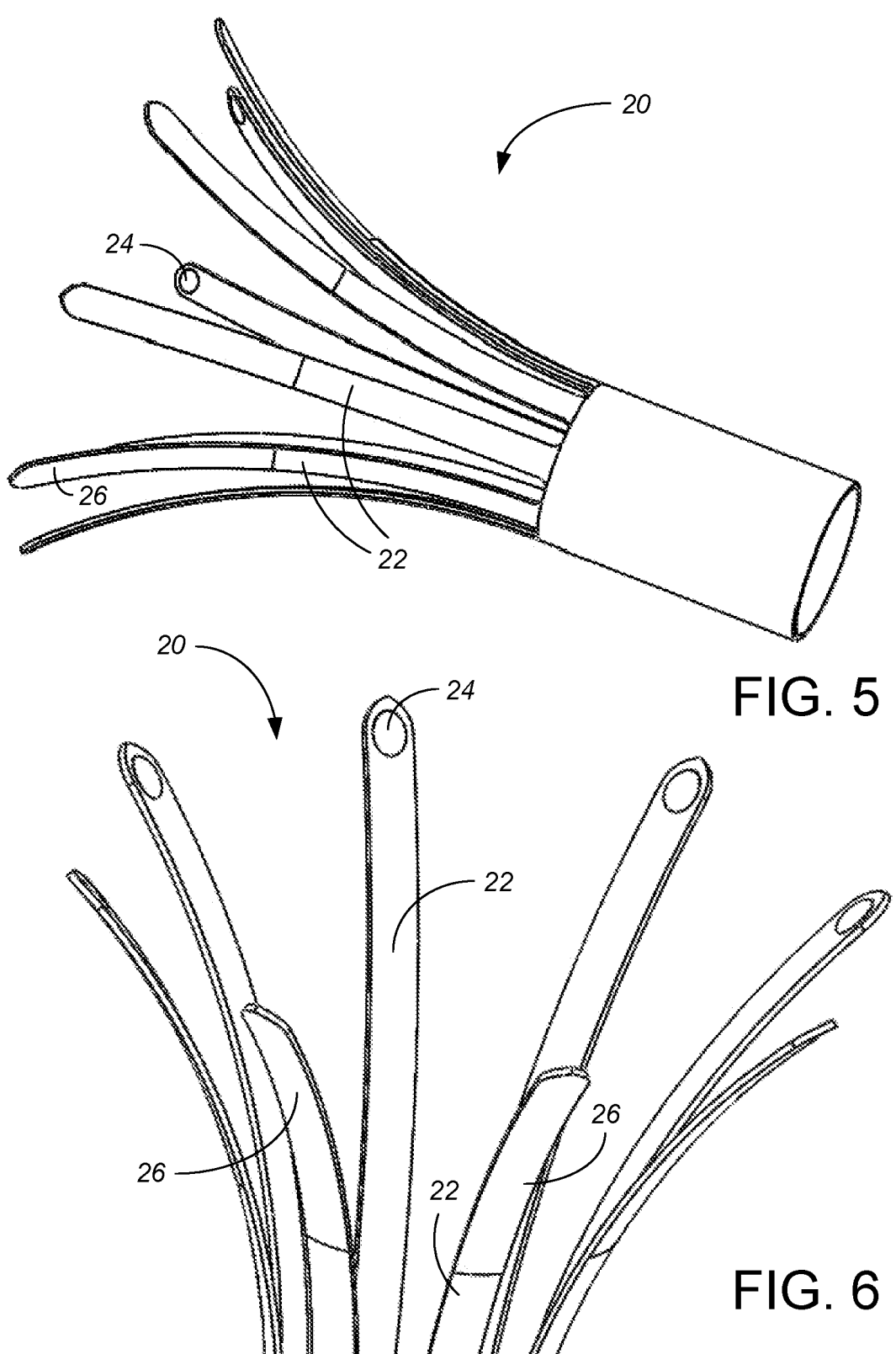
FIG. 5 is a perspective view of a cut and formed hypotube in accordance with the present invention.
FIG. 6 is a perspective view of the end of the hypotube of FIG. 5, taken from a different perspective.
Figures 7, 8:
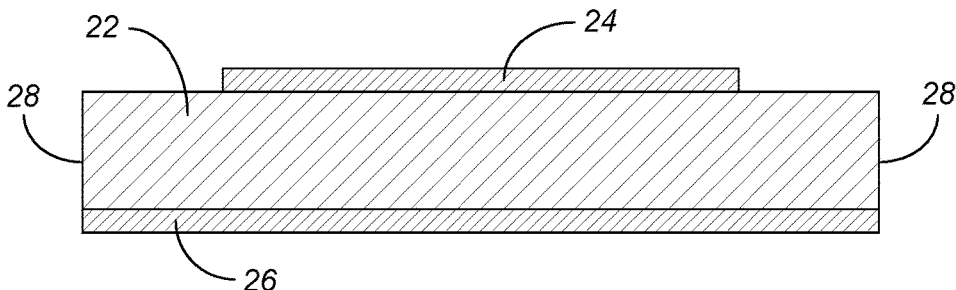
FIG. 7 is an enlarged perspective view of a portion of the hypotube of FIGS. 5 and 6.
FIG. 8 is a cross-sectional view of a portion of the hypotube of FIGS. 5-7, taken along the cut lines 8-8 in FIG. 7.
Figure 9:
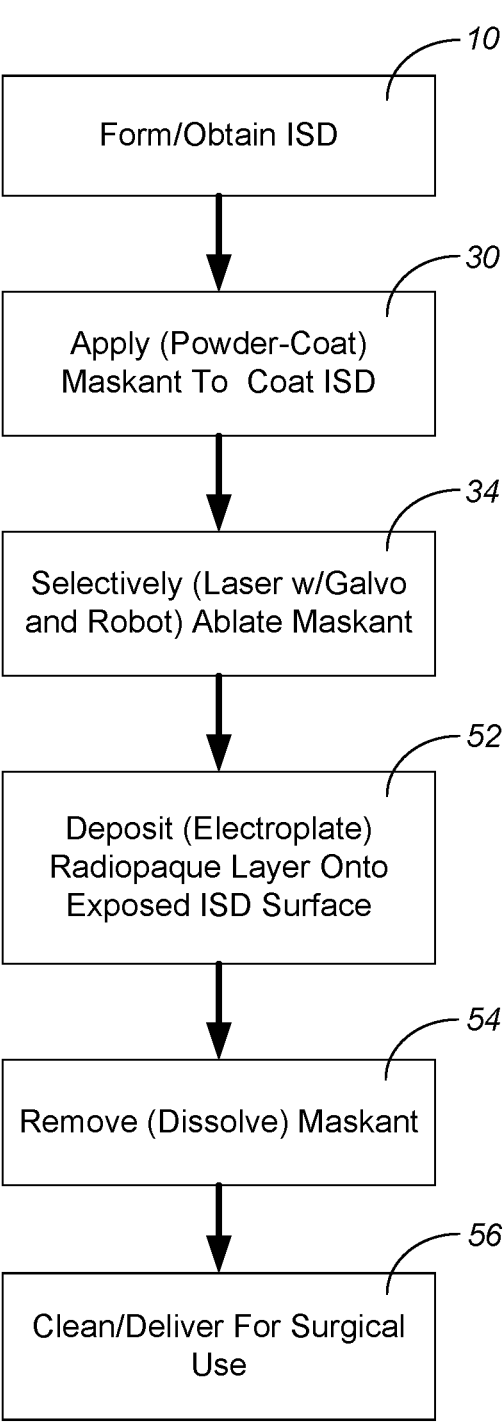
FIG. 9 is a flow chart explaining the method of the present invention.
Figure 10:
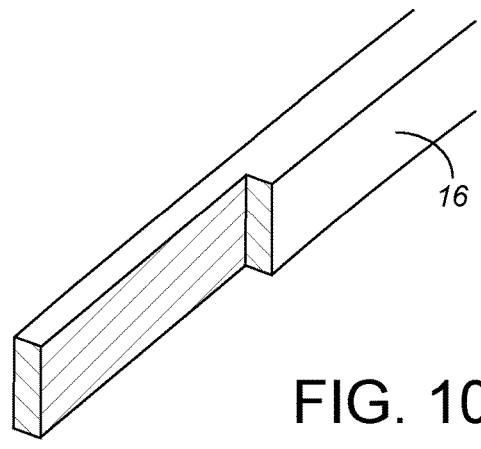
FIG. 10 is a partially perspective, partially cross-sectional view of a portion of an interventional surgical device (such as the portion shown in FIG. 4) prior to the present invention.

FIGS. 3 and 4 depict portions of the stent 12 of FIGS. 1 and 2 having radiopaque marker layer strips 18 in accordance with the present invention. FIG. 3 shows four marker strips 18 on the stent 12. In this particular example, all four of the marker strips 18 are at an end of the stent 12, on the final segment of the elastic strands or beams 14/16. Each marker strip 18 runs only on one side of the elastic strand/beam 14/16, the side facing radially outward on the stent 12. Each marker strip 18 is the full width of the elastic strand/beam 14/16, for about the middle third of the length of the final segment 16, and at a thickness significantly less than the thickness of the elastic strand/beam 14/16. Two of the marker strips 18 are adjacent each other, whereas the other two marker strips 18 are at other edges of the stent 12. The preferred embodiment similarly places four marker strips at the opposite end of the stent 12 (such marker strips not shown), i.e., the opposite end of this particular stent 12, turned around 180°, would look identical to FIG. 3. The marker strips 18 are of a material having a radiodensity which is different than the radiodensity of the stent material. Preferred marker strip materials are tungsten, gold, platinum, iridium, osmium, tantalum and rhenium, and alloys thereof, preferably platinum or more preferably gold when on a stent 12 formed of nitinol. The four marker strips 18 (or eight marker strips on the entire stent 12) can thus be used by the surgeon under common imaging systems to visually identify, with a high degree of precision, not only the end(s) of the stent 12 but also the longitudinal axis and outer diameter of the stent 12, both before and after deployment release of the stent 12. Even at deployment locations where one or more of the marker strips 18 may be shrouded on the imaging system due to the radiopacity of surrounding tissue, the appearance of the other marker strips 18 on the imaging system is sufficient for the surgeon to precisely understand the location of the stent 12 relative to the human tissue at any given instant during the surgical placement of the stent 12. While longitudinal position is frequently most critical, use of multiple marker strips 18 can also enable the surgeon to determine the expansion state (i.e., effective diameter at any given moment) of the stent 12. An added benefit is that, by locating marker strips 18 asymmetrically about the radial axis, the surgeon can determine the rotational orientation of the ISDFU FIGS. 5-8 depict a different type of ISDFU, a hypotube 20, using the present invention. This hypotube 20 includes eight fingers 22 that bend or flex outwardly from the longitudinal axis of the hypotube 20 during use, so the primary flexing direction is once again radially inward/outward. The base hypotube 20 can be formed, for instance, by laser cutting a stainless steel, or other biocompatible alloy or more preferably a nitinol tube, having a wall thickness preferably in the range of 0.010 to 0.015 inches. Eight circular radiopaque markers 24 are placed one each on the inner side of each finger 22, at the end of the finger 22 but leaving a margin around each circular marker 24. On the outer of each finger 22, the distal half of each finger 22 is completely covered by a thin radiopaque coating layer 26. The side edges 28 of each finger 22 are fully exposed, i.e., not covered with any radiopaque material. The eight circular markers 24 and the eight coating layers 26 have a thickness thinner than the wall thickness of the hypotube 20. The eight circular markers 24 and the eight coating layers 26 can be used by the surgeon under common imaging systems to visually identify, with a high degree of precision, both the end location of each finger 22 and the curvature of each finger 22 at each instant during use of the hypotube 20. For instance, depending upon the imaging system being used, the thickness of the eight circular markers 24 and the eight coating layers 26 can be in the range of 0.0003 to 0.002 inches.

Further understanding of the patterned metal markers on ISDFUs is provided with an explanation of the preferred method of the present invention with respect to FIGS. 9-16. In each case, the design and formation/fabrication of the base ISDFU is achieved as a first step 10, without regard to the patterned metal markers 18, 24, 26. The patterning (i.e., location, shape, areal size and thickness) of the patterned metal markers 18, 24, 26 is then determined and achieved separately for each base ISDFU or batch of base ISDFUs.

Figure 11:
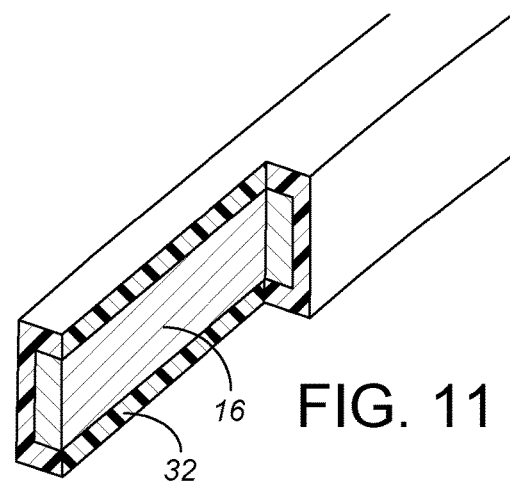
FIG. 11 is a partially perspective, partially cross-sectional view of the portion of the interventional surgical device of FIG. 10, after application of the maskant.

For any portion of the base ISDFU on which the patterned metal marker will be applied, the next step 30 is to apply maskant 32 over the entire exposed surface of the base ISDFU as shown in FIG. 11. The maskant 32 is a non-metal material coating which should be a) significantly more easily removed, in a carefully controlled profile, by the CNC subtractive material removal method employed, than the material of the base ISDFU; b) chemically insoluble in the electroplating conditions to which it will be exposed; and c) fully removable (together with any overlapping metal layer) via a separate removal method. More preferably, the maskant 32 is a polymeric layer material which after curing remains soluble in a solvent. For instance, the preferred maskant 32 is an epoxy coating, with the most preferred epoxy coating being ESS-4441 Flatter Black high adhesion powder coat available from Prismatic Powders of White City, Oregon. The powder coating 32 is electrostatically sprayed onto a cold metallic substrate and then thermoset or cured, such as at a temperature of 400° F. (substrate temperature) for 10 minutes. The preferred powder coating 32 is applied at a thickness in the range of 0.001-0.010 inches, and more preferably in the range of 0.003-0.005 inches. After curing, the powder coating 32 remains soluble in methylene chloride, acetone, methyl ethyl ketone and possibly other REACH-compliant solvents (REACH is a set of European Union regulations standing for "Registration, Evaluation, Authorisation and restriction of CHemicals").

After the maskant 32 has been cured or otherwise hardened over the entire surface of the base ISDFU which will be subject to metal deposition, the next step 34 of the process is to selectively remove one or more selected, targeted portions of the maskant 32 by a computer-numerically-controlled (CNC) subtractive process. The preferred CNC controlled subtractive process is laser ablation, using the ablation system 36 shown in FIG. 12. The ablation system 36 includes a laser 38, a galvo 40 and a robot 42, all operating under control of a CNC controller 44. In the preferred embodiment, the laser beam 46 is directed through a controlled beam expander 48 and two controlled mirrors 50 on its way to the galvo 40. In the most preferred system configuration, the diameter of the laser beam 46 can be controlled in a diameter range of about 0.001-0.010 inches on the part 12/20. The layout of the beam expander 48 and the mirrors 50 control the width of the laser beam 46 as it reaches the galvo 40 and the part 12/20. The galvo 40 is a galvanometer-based, small beam diameter scanning mirror system which then allows for fine, controlled movement of the laser beam 46 onto the part 12/20. In the most preferred system 36, the galvo 40 can steer the laser beam 46 up to about 0.4 inches. The robot 42 holds the part 12/20 and allows for larger movements of the part 12/20, and importantly, manipulates the part 12/20 through 3-dimensional space so the surface portion being ablated is normal to the laser beam 46 from the galvo 40 and close to the focal length of the beam 46 as it exits the galvo optics. In the most preferred system 36, the robot 42 is a 6-axis robot 42 which can move the part 12/20 with an accuracy of about +−0.003 inches. Using the galvo 40 together with the robot 42 allows for more accurate and faster ablation than merely using the robot 42 alone.

The type and amplitude of the laser 38 is preferably selected in conjunction with the material and thickness used for the maskant 32 and the underlying material of the ISDFU. For the preferred epoxy powder coat maskant materials, the laser 38 should have enough power and energy to break down C—C and C—H bonds at higher repetition rates for fast micromachining. Higher amplitude of the laser results in a more "kinetic" ablating of the polymer, which reduces residue and subsequent cleaning demands. Preferred embodiments use either a doped laser or an excimer laser, providing a UV rather than IR light wavelength, such as at a wavelength less than about 500 nm. Excimer lasers have issue of maintaining Florine based gases (safety issues) and are expensive systems for long time use in industrial settings. They are operated at higher frequency and shorter wavelength compared to solid state systems. For instance, the laser 38 can be: a) an ArF excimer laser at a wavelength of 193 nm; b) a KrF excimer laser at a wavelength of 248 nm; c) a Nd YAG (4$^{th}$ Harmonic) laser at a wavelength of 266 nm (there are commonly some stability issues in terms of laser output in 266 nm systems); d) a XeF excimer laser at a wavelength of 351 nm; or e) an Nd YAG (3$^{rd}$ harmonic or tripled) laser at a wavelength of 355 nm; and most preferably f) a solid state laser Nd YVO (4$^{th}$ Harmonic) laser at a wavelength of 335 nm. In the most preferred solid state system, the pulse width and energy of each pulse can be precisely defined.

Figure 13:
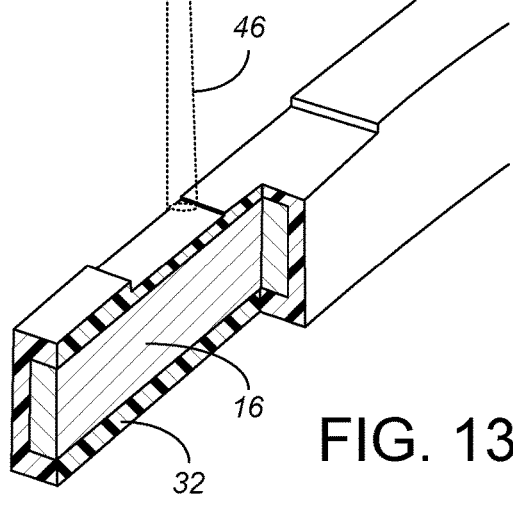
FIG. 13 is a partially perspective, partially cross-sectional view of the portion of the interventional surgical device of FIGS. 10 and 11, during ablation of the maskant.
Figure 14:
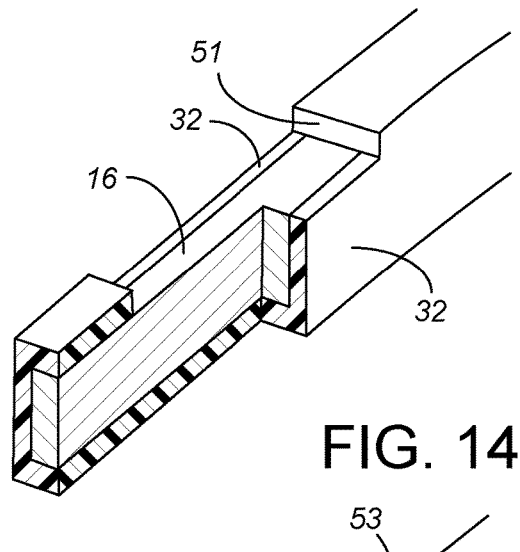
FIG. 14 is a partially perspective, partially cross-sectional view of the portion of the interventional surgical device of FIGS. 10, 11 and 13, after ablation of the maskant.
Figure 15:
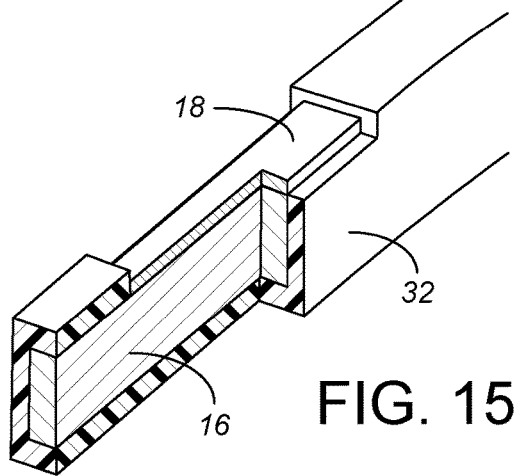
FIG. 15 is a partially perspective, partially cross-sectional view of the portion of the interventional surgical device of FIGS. 10, 11, 13 and 14, after deposition of the marker segment.

Using the preferred laser 38 and maskant 32, the laser beam 46 ablates about 0.0005-0.001 inches of maskant depth per pass (on a surface normal to the beam 46) as shown in FIG. 13, and thus complete removal of a targeted area of the maskant 32 may require multiple passes of the ablation laser beam 46 as moved by the galvo 40. Assuming the ISDFU is formed of a metal such as nitinol or stainless steel, the laser beam 46 ablates the preferred maskant 32 at a rate which at least an order of magnitude (believed to be 10-100 times faster) than the underlying nitinol/stainless steel. The removal rate depends on the type of laser 38 and power being used, as well as the diameter of the laser beam 46 under control of the beam expander 48, which in the preferred system can expand the laser beam 46 up to a maximum diameter of about 10 mm. Under the CNC control, the ablation continues until the maskant 32 is removed just in the target locations for the (radiopaque) metal layer application, but cleanly and fully removed in those locations as shown in FIG. 14. In the example shown, this is about a 0.040 inch length along a single side of the elastic strand/beam 14/16, with each elastic strand/beam 14/16 having a length of 0.050 inches or more between adjacent intersections of strand/beams 14/16. The removal of maskant 32 for each patterned metal marker location is accomplished by control of the galvo 40 while the robot 42 holds the ISDFU stationary, with the robot 42 then moving and/or turning the ISDFU to a new position for the next patterned metal marker location.

Depending upon the accuracy needed, the preferred laser/galvo/robot system 36 could be replaced with different CNC material removal equipment, such as a CNC mill (not shown) using cutting tools (not shown). However, the preferred laser/galvo/robot system 36 provides high accuracy desired for markers on most ISDFUs. Importantly, the CNC targeted maskant removal system 36 allows maskant removal on only one side of each elastic strand/beam 14/16, leaving maskant 32 on the other three sides (for a rectangular cross-sectioned strand/beam 14/16) as shown in FIG. 14.

The material selected for the maskant 32 should preferably, after conclusion of removing (ablating) the selected maskant areas, maintain edge walls 51 which are as sharp and vertical as possible, with no edge lift or separation from the underlying ISDFU particularly at edges 51. Choice of powder coat material is critical to maintaining excellent adhesion and integrity throughout maskant removal.

After all of the patterned metal marker locations have been removed (ablated) from the masked ISDFU, the next step 52 is deposition of a metal layer 18, 24, 26. While the metal layer 18, 24, 26 could be deposited by other methods such as physical vapor deposition (PVD, also sometimes called Chemical Vapor Deposition, or sputtering) or electroless deposition, the preferred method involves electrolytic deposit, which deposits the metal layer 18, 24, 26 an order of magnitude (estimated at about 10 times) faster than PVD. While the preferred powder coating 32 is applied at least over the entire surface of the base ISDFU which will be subject to metal deposition, if electrolytic deposition is used to apply the metal layer, a further proximal location (not shown) on the base ISDFU may also be exposed from maskant 32, either by shielding a proximal portion of the base ISDFU during the maskant application step 30, or by ablating an additional area on the maskant 32 during the ablation step 34. That proximal location is then kept out of the electrolytic solution for attachment of an electrode during the metal deposition step 52. Alternatively, if the ISDFU features an inner diameter such as would be present in a hypotube, then electrical contact with the ISDFU can be accomplished by means of an electrode (not shown) inserted into the inner diameter of the ISDFU.

For the preferred marker strips 18 shown in FIGS. 3, 4, 15 and 16, the radiopaque metal is deposited at a thickness great enough to readily be seen on common ISDFU visualization systems, but thin enough to remain thinner than the maskant 32. In the preferred embodiments of depositing gold onto nitinol ISDFUs, this is an electrodeposited gold layer 18 of 0.0003-0.002 inches thick. Because the preferred maskant 32 is electrically insulative, the electrodeposition occurs only on the exposed portions of the ISDFU and not on the maskant-covered portions of the ISDFU.

The excellent adhesion and integrity of the maskant 32, particularly at the edges 51, allows for correspondingly sharp and vertical edges 53 of the metal layer 18, 24, 26, producing the metal layer 18, 24, 26 with no "run out" at the edges 53. "Run out", which can also be referred to as "edge bleed", is an extremely thin layer of deposited metal extending away from the marker edge 53. This run out metal may be poorly adhered to the ISDFU and susceptible to flaking or breaking free, which in the case of a stent or hypotube could create an embolism risk. Choice of powder coat material is critical to maintaining excellent adhesion during the electroplating sequence. For instance, the preferred embodiments produce edges 53 where the greatest run out is less than the thickness of the metal layer 18, 24, 26 (i.e., for a 0.002 inch thick metal layer 18, 24, 26, the worst run out location extends less than 0.002 inches laterally from the top corner of the edge 53), and more preferably edges 53 where the greatest run out is less than 30% of the thickness of the metal layer 18, 24, 26, such as a maximum run out of 0.001 inches or less.

Figure 16:
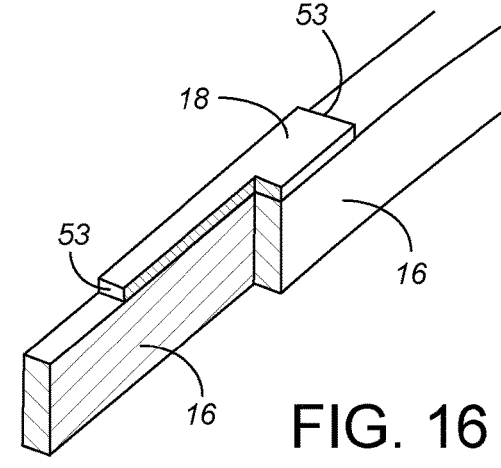
FIG. 16 is a partially perspective, partially cross-sectional view of the portion of the interventional surgical device of FIGS. 10, 11 and 13-15, after removal of the maskant.
Figure 12:
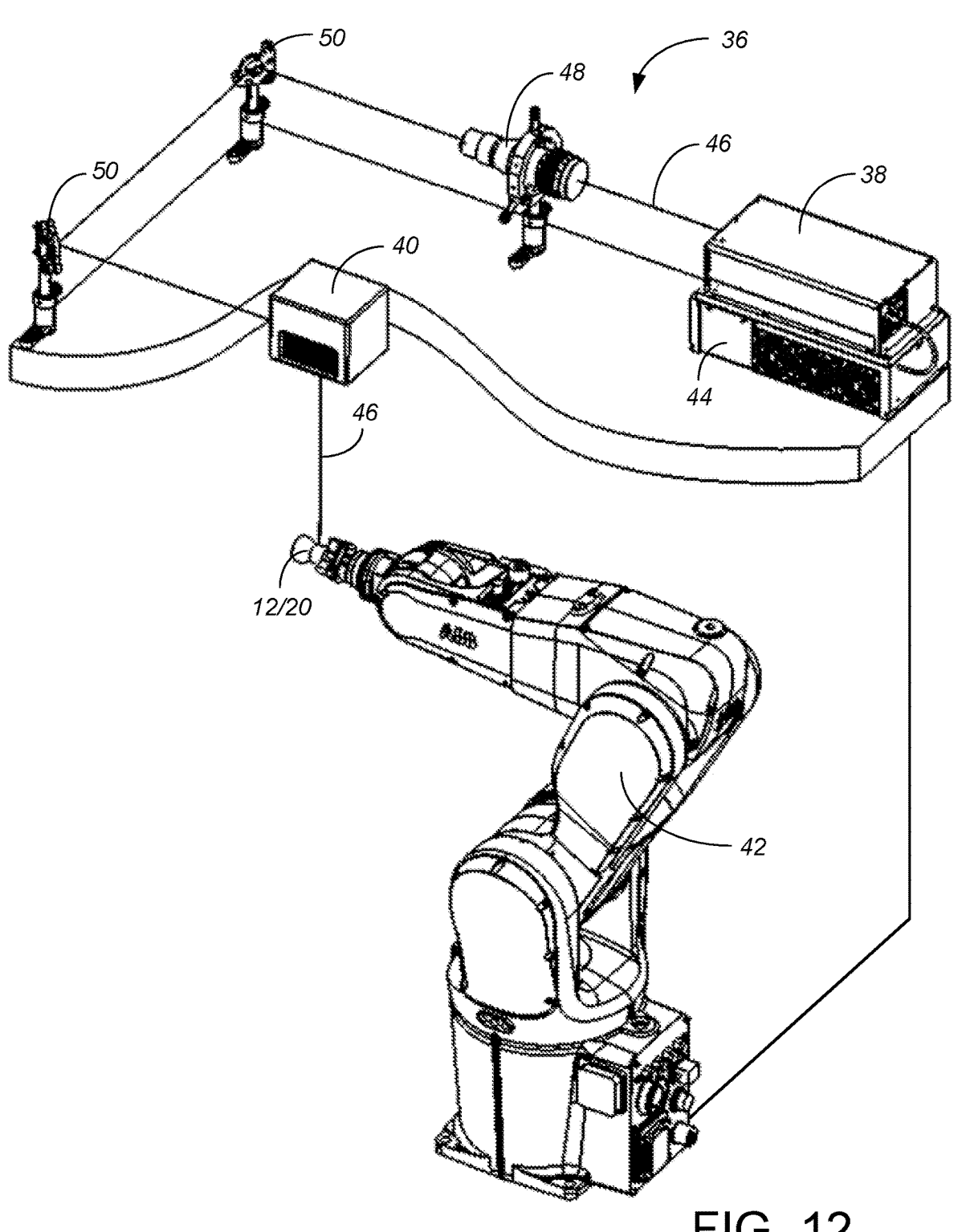
FIG. 12 is a perspective view of a system in accordance with the present invention during ablation of the maskant.

The next step 54 is to remove all remaining maskant 32, as shown in FIG. 16. Removal of the maskant 32 can be via thermal reduction or chemical dissolution, and the most preferred method dissolves the maskant 32 in a REACH-compliant solvent.

The final step 56 is any further cleaning or disinfecting, and then providing the ISDFU 12, 20 with markers 18, 24, 26 for further assembly into a catheter system and surgical use.

The described method results in the ISDFU parts 12/20 such as shown in FIGS. 3-7. Because the maskant layer 32 (where not CNC/laser removed) was thicker than the deposited metal layer 18, 24, 26, with good squareness of the edges 51 of the maskant 32, the edges 53 of the marker 28, 24, 26 will be generally perpendicular to the surface of the ISDFU 12/20. there is no edge lift issues associated with the marker locations. The markers 18, 24, 26 can be carefully targeted with clean edges and little to no run out, which will not flake or break off during ordinary surgical use and/or implantation. Importantly, the resultant markers 18, 24, 26 can be deposited on only one side of the strand/beams 14/16 or fingers 22, without circumscribing any portion of the ISDFU. Therefore the resultant markers 18, 24, 26 do not impede the flexing of the ISDFU 12, 20 nearly as much as prior art markers would. The preferred markers 18, 24, 26 orient their thinnest dimension (the thickness of the metal material) in the primary flexing direction, providing little resistance to flexing, and the resultant ISDFU 12, 20 flexes during use much more the way the ISDFU designer intended. The radiopaque markers 18, 24, 26 provide maximum accuracy in surgical visualization, while minimizing any effect of flexing of the ISDFU 12,20.

Although the present invention has been described with reference to preferred embodiments, workers skilled in the art will recognize that changes may be made in form and detail without departing from the spirit and scope of the invention. For instance, while the preferred method is primarily intended to place radiopaque markers on ISDFUs (without circumscribing any portion of the ISDFU), other applications of the inventive method would allow thin and small patterned metal layer placement onto an ISDFU for other purposes (for instance, for use as an electrically conductive pad irrespective of radiodensity). The preferred method could further be used onto a surgical implant which does not flex during use, such as on a surgical needle, such as a small spot of radiopaque material positioned about 0.018 inches from the bevel edge of the needle, so the surgeon can better visualize when performing internal tissue sewing/stitching. The preferred method may even have applications outside the field of surgical devices.

What is claimed is:

1. A method of forming an interventional surgical device which flexes during use (ISDFU), comprising:
   providing a base ISDFU, wherein the base ISDFU is a stent formed of a plurality of nitinol strands and/or beams;
   coating at least a portion of the base ISDFU with a maskant, the maskant being of a different material than the base ISDFU;
   computer numerically controlled (CNC) removing of selected areas of the maskant to expose selected areas of the base ISDFU within the remainder of the maskant;
   depositing a metal layer onto the exposed selected areas of the masked base ISDFU; and
   removing the remainder of the maskant while leaving the deposited metal layer intact on the selected areas of the base ISDFU, wherein the deposited metal layer left intact on the selected areas of the base ISDFU does not circumscribe any of the nitinol strands and/or beams.

2. The method of claim 1, wherein the computer numerically controlled removing of selected areas of the maskant comprises ablation of the maskant, and wherein the selected areas minimally affect flexing of the base ISDFU.

3. The method of claim 2, wherein the ablation of the maskant is achieved with a laser beam.

4. The method of claim 3, wherein the computer numerically controlled removing of selected areas of the maskant comprises moving the masked base ISDFU relative to the laser beam.

5. The method of claim 4, wherein the laser beam is steered with a CNC galvo.

6. The method of claim 5, wherein the masked base ISDFU is moved with a CNC robot.

7. The method of claim 1, wherein the maskant is an electrostatically sprayed epoxy powder coating, and further comprising curing the electrostatically sprayed epoxy powder coating.

8. The method of claim 1, wherein the metal layer is deposited by electrolytic plating.

9. The method of claim 1, wherein the deposited metal layer is a radiopaque material selected from the group consisting of tungsten, gold, platinum, iridium, osmium, tantalum and rhenium, and alloys thereof.

10. The method of claim 1, wherein the coating is thicker than the deposited metal layer.

11. The method of claim 7, wherein the removing the remainder of the maskant is by dissolving the maskant in a solvent.

12. A method of forming an interventional surgical device which flexes during use (ISDFU), comprising:
   providing a base ISDFU, wherein the base ISDFU is a stent formed of a plurality of strands and/or beams formed of nitinol or stainless steel;
   coating at least a portion of the base ISDFU with a maskant, the maskant being of a different material than the base ISDFU;
   computer numerically controlled (CNC) removing of selected areas of the maskant to expose selected areas of the base ISDFU within the remainder of the maskant, wherein each selected area covers only one side of its strands and/or beams, for a length less than the distance between adjacent intersections of its strands and/or beams;
   depositing a metal layer onto the exposed selected areas of the masked base ISDFU; and
   removing the remainder of the maskant while leaving the deposited metal layer intact on the selected areas of the base ISDFU.

13. The method of claim 11, wherein the maskant is a powder coating of polymer to form a powder coated base ISDFU.

14. The method of claim 13, wherein the polymer is epoxy, and wherein the metal layer is a radiopaque material selected from the group consisting of tungsten, gold, platinum, iridium, osmium, tantalum and rhenium, and alloys thereof.

15. The method of claim 12, wherein the computer numerically controlled (CNC) removing is with a laser beam steered with a computer numerically controlled (CNC) galvo.

16. The method of claim 13, wherein computer numerically controlled (CNC) removing involves moving the powder coated base ISDFU relative to a laser beam with a computer numerically controlled (CNC) robot.

17. The method of claim 12, wherein the metal layer is deposited using electroplating.

18. The method of claim 12, wherein a thickness of the metal layer deposited onto the exposed selected areas of the base ISDFU is within the range of 0.0003-0.002 inches.

* * * * *